US012746409B2

(12) United States Patent
Kim et al.

(10) Patent No.: US 12,746,409 B2
(45) Date of Patent: Sep. 29, 2026

(54) LASER IRRADIATION DEVICE FOR MEDICAL TREATMENT

(71) Applicant: WONTECH Co., Ltd., Daejeon (KR)

(72) Inventors: Jong Won Kim, Seongnam-si (KR); Jung Hyun Kim, Seongnam-si (KR); Young Seok Seo, Sejong-si (KR)

(73) Assignee: WONTECH Co., Ltd., Daejeon (KR)

( * ) Notice: Subject to any disclaimer, the term of this patent is extended or adjusted under 35 U.S.C. 154(b) by 128 days.

(21) Appl. No.: 18/589,224

(22) Filed: Feb. 27, 2024

(65) Prior Publication Data

US 2024/0285966 A1 Aug. 29, 2024

(30) Foreign Application Priority Data

Feb. 28, 2023 (KR) ........................ 10-2023-0026459

(51) Int. Cl.
*A61N 5/06* (2006.01)

(52) U.S. Cl.
CPC .... *A61N 5/0616* (2013.01); *A61N 2005/0627* (2013.01); *A61N 2005/0632* (2013.01); *A61N 2005/0644* (2013.01); *A61N 2005/0664* (2013.01)

(58) Field of Classification Search
CPC .......... A61N 5/0616; A61N 2005/0627; A61N 2005/0632; A61N 2005/0644; A61N 2005/0664; A61N 5/067; A61B 18/20; A61B 2018/00452; A61B 2018/00458; A61B 2018/20359; A61B 2018/205545; A61B 2018/205547; A61B 18/203; A61B 34/10; A61B 90/361; A61B 2018/00898; A61B 2018/20351; A61B 2034/107
See application file for complete search history.

(56) References Cited

U.S. PATENT DOCUMENTS

| | | | | |
|---|---|---|---|---|
| 8,908,904 B2 * | 12/2014 | Santos | H04N 23/80 | 382/118 |
| 2002/0049432 A1 * | 4/2002 | Mukai | A61B 18/203 | 606/9 |
| 2005/0154382 A1 * | 7/2005 | Altshuler | A61B 18/203 | 606/9 |
| 2015/0057622 A1 * | 2/2015 | Hyde | G06F 16/2455 | 604/289 |

(Continued)

FOREIGN PATENT DOCUMENTS

| | | |
|---|---|---|
| JP | 2003-339753 A | 12/2003 |
| KR | 10-0720868 B1 | 5/2007 |

(Continued)

OTHER PUBLICATIONS

KR Office Action.

*Primary Examiner* — David Hamaoui
*Assistant Examiner* — Olivia Walker
(74) *Attorney, Agent, or Firm* — Harvest IP Law, LLP

(57) ABSTRACT

Proposed is a laser irradiation device for medical treatment for irradiating a laser treatment target with a laser beam. The device includes a handpiece configured to irradiate the laser treatment target with a laser beam in a preset guide shape, and a controller configured to set, on the basis of data on the laser treatment target, a guide shape for emitting a laser beam and generate a control message to control an operation of the handpiece on the basis of the guide shape.

9 Claims, 7 Drawing Sheets

(56) References Cited

U.S. PATENT DOCUMENTS

| | | | | |
|---|---|---|---|---|
| 2018/0014777 | A1* | 1/2018 | Amir | A61M 35/003 |
| 2018/0111003 | A1* | 4/2018 | Hewitson | A61B 18/203 |
| 2019/0244274 | A1* | 8/2019 | Chang | G06V 40/171 |
| 2019/0357976 | A1* | 11/2019 | Youngquist | A61N 5/0616 |
| 2023/0064129 | A1* | 3/2023 | Hunziker | G16H 50/20 |

FOREIGN PATENT DOCUMENTS

| | | | |
|---|---|---|---|
| KR | 10-2018-0102031 | A | 9/2018 |
| KR | 10-2019-0064273 | A | 6/2019 |

* cited by examiner

LASER IRRADIATION DEVICE FOR MEDICAL TREATMENT

CROSS REFERENCE TO RELATED APPLICATION

The present application claims priority to Korean Patent Application No. 10-2023-0026459, filed Feb. 28, 2023, the entire contents of which is incorporated herein for all purposes by this reference.

BACKGROUND OF THE INVENTION

Field of the Invention

The present disclosure relates to a device and, more particularly, to a laser irradiation device for medical treatment.

Description of the Related Art

In general, laser treatment using lasers is widely known for treating skin problems and conditions such as freckles, age spots, and blemishes. Currently, as a new skin treatment using lasers, a method of creating hundreds to thousands of microscopic treatment zones in the skin and performing laser treatment on each microscopic treatment zone is gaining popularity.

Laser irradiation of hundreds to thousands of microscopic treatment zones is carried out by forming multiple laser spots on a treatment target, and conventionally, the laser spots are formed using a laser scanner device. However, since the laser scanner device does not form multiple spots at the same time, but forms multiple spots with a time difference, the laser scanner device has the disadvantage of making it difficult to perform treatment quickly and is not easy to operate.

Recently, a laser device system that implements multiple spots using a microlens array has been introduced (Korean Patent No. 0720868). This is a technology that creates multiple spots by forming a plurality of microlens arrays and passing a laser beam through the arrays, so that a large number of beams are emitted. However, in this case, forming a microlens array and adjusting the spot size or laser intensity are not easy. Moreover, since the laser intensity for individual spots in the entire irradiation area is not uniform, effective treatment is difficult to achieve.

Meanwhile, the above-mentioned conventional laser equipment for medical treatment uses beams provided by means of a resonator in an optics unit to treat a patient's affected area. Especially, in the treatment range of 500 to 3,000 nm, which is the near-infrared wavelength treatment range of medical laser equipment, the shape of the beam generated by configuring a laser resonator to be used as a therapeutic laser is a circular with a diameter of about 0.5 to 15 mm. In addition, the beam is formed as a centrally focused Gaussian beam (TEM00) or is formed to have uniform fluence like a TopHat beam.

However, in traditional laser treatment, a method of direct emission of the beams provided through the resonator in the optical unit has the disadvantage of long downtime and slow regeneration. Accordingly, a new type of fractional laser system with a short treatment time, less pain, and rapid regenerative effects has become necessary.

While the fractional laser system has the advantage of being able to irradiate the skin evenly and requiring a short treatment time, the emission range is not constant and refraction occurs depending on the light entering a lens. In order to solve these problems, a lens that can emit light to the desired point regardless of the angle at which the light enters is inserted and used. The problem is that depending on the size of the laser and the irradiation range, there are laser blind spots on the skin that cannot be irradiated.

SUMMARY OF THE INVENTION

Accordingly, the present disclosure has been made keeping in mind the above problems occurring in the related art, and the present disclosure is intended to provide a laser irradiation device for medical treatment that enables a user to set the desired shape of a laser beam, the number and intensity of laser beams delivered by range, and is capable of irradiating the skin, even to laser blind spots on the skin that could not be irradiated by finely adjusting the shapes of laser beams.

Objectives of the present disclosure are not limited thereto, and other objectives not mentioned will be clearly understood by those skilled in the art from the following description.

In order to achieve the above objective, according to an embodiment of the present disclosure, there is provided a laser irradiation device for medical treatment for irradiating a laser treatment target with a laser beam, the device including: a handpiece configured to irradiate the laser treatment target with a laser beam in a preset guide shape; and a controller configured to set, on the basis of data on the laser treatment target, a guide shape for emitting a laser beam and generate a control message to control an operation of the handpiece on the basis of the guide shape.

In this case, the handpiece may include: a scanner that is disposed inside the handpiece, includes at least one mirror, and determines a location where the laser beam is emitted on the basis of the preset guide shape.

In this case, the handpiece may further include: an imaging part that is disposed on an outside the handpiece, and acquires medical image data by photographing a face of the laser treatment target; and a motion sensor module that is disposed on a side of the handpiece, detects movement of the handpiece, and acquires motion data.

In this case, the data on the laser treatment target may include at least one of a treatment case of the treatment target that has already been stored or newly input, medical image data of the treatment target, and treatment conditions of the treatment target.

In this case, the controller may extract position coordinate values of individual facial components from the medical image data, and set a plurality of facial areas using the extracted position coordinate values.

In this case, the controller may distinguish between an irradiation area and a non-irradiation area from the facial areas, and set, in a circular or polygonal laser beam shape, a shape excluding the non-irradiation area as a guide shape for delivering a laser beam.

In this case, the scanner may further include: a mirror drive part connected to the mirror and changing a position and an angle of the mirror, wherein the mirror drive part may receive the control message from the controller and adjust the position and the angle of the mirror to a preset position and angle according to the guide shape.

In this case, the controller may recognize at least one facial area where a laser treatment has been completed from the plurality of facial areas on the basis of the acquired motion data.

In this case, the controller may establish a treatment plan for each area of the plurality of facial areas, wherein the treatment plan may be a planned sequence for each of the facial areas so that a first facial area where a first laser treatment is completed and a second facial area where a second laser treatment will be performed after the first laser treatment do not overlap.

In this case, the handpiece may further include: a notification part that is disposed on the outside the handpiece, and provides notifications to an outside using sound or light, and the controller may transmit a control message to the notification part to provide notifications when a position coordinate value of a first facial area where a first laser treatment is completed and a position coordinate value of a second facial area where a second laser treatment will be performed after the first laser treatment overlap.

As described above, according to embodiments and various aspects of the present disclosure, since the shape, irradiation range, number, intensity, etc., of laser beams required according to a patient's condition can be set, side effects due to individual skin conditions can be minimized.

Furthermore, according to the present disclosure, since the beam shape and laser intensity can be finely adjusted corresponding to the location and shape of various treatment target areas to deliver lasers without laser blind spots, treatment effect can be improved.

The effects of the present disclosure are not limited to the above effects, but should be understood to include all effects that may be inferred from the configuration of the invention described in the description or claims of the present disclosure.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION OF THE INVENTION

Figure 1:
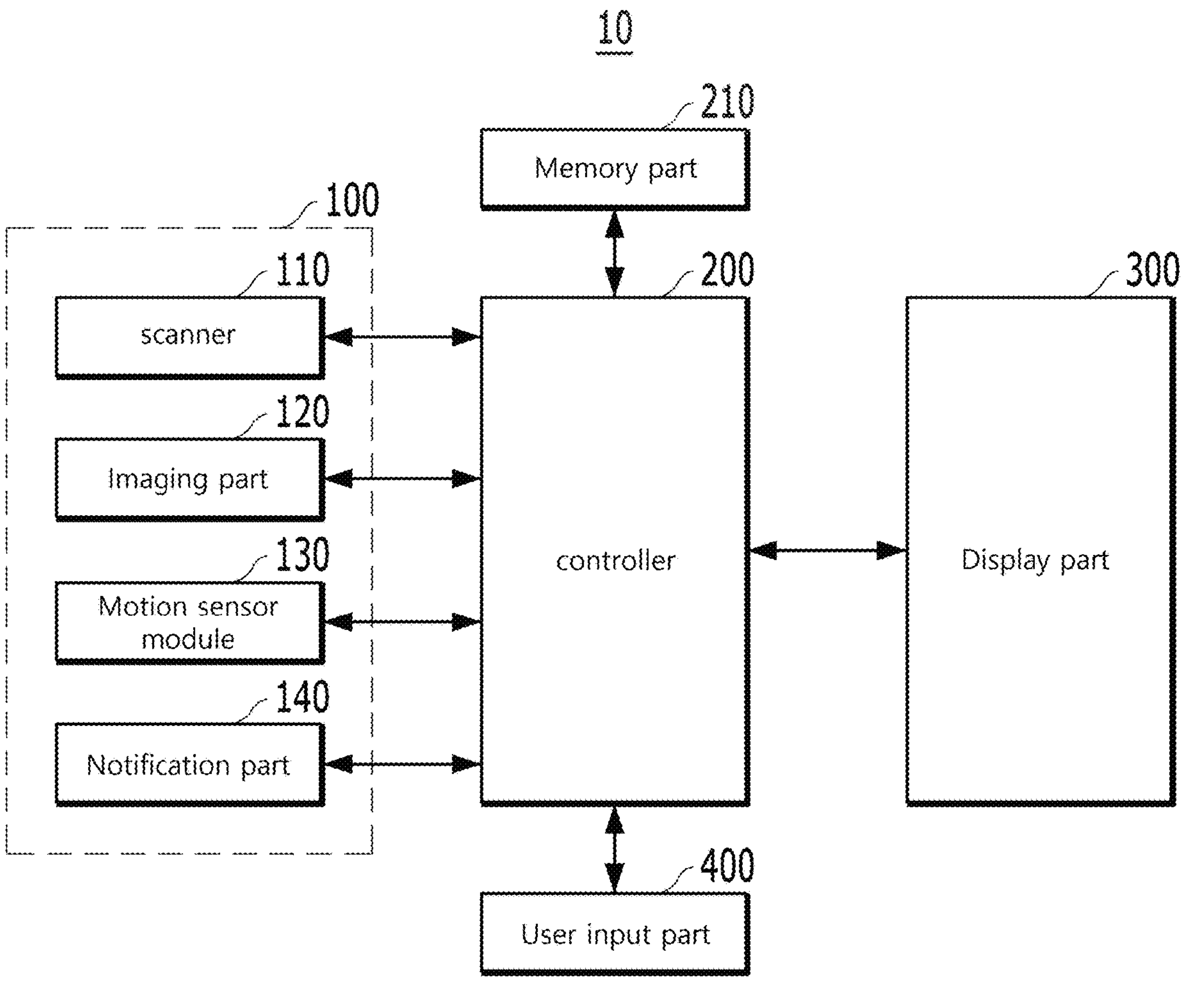
FIG. 1 is a block diagram showing a laser irradiation device for medical treatment according to an embodiment of the present disclosure.

Hereinafter, the present disclosure will be described in detail with reference to the accompanying drawings. The present disclosure may be implemented in several different forms, and the scope of the present disclosure is not limited to the following embodiments. In addition, in order to clearly explain the present disclosure, parts not related to the description have been omitted in the drawings, and similar reference numerals are given to similar parts throughout the specification.

Throughout the specification, when a part is said to be "connected (contacted, combined)" with another part, this means not only when it is "directly connected" but also when it is "indirectly connected" with another member in between. In addition, when a part "comprises (includes)" a certain component, this means that other components may be further included, not excluding other components, unless specifically stated to the contrary.

The terminology used herein to describe embodiments of the present disclosure is not intended to limit the present disclosure. The singular expression includes the plural expression unless the context clearly dictates otherwise. It will be further understood that the terms such as "comprise (include)" or "have", when used herein, specify the presence of stated features, numbers, steps, operations, elements, and/or components but do not preclude the presence or addition of one or more other features, numbers, steps, operations, elements, components, and/or groups thereof.

Hereinafter, embodiments of the present disclosure will be described in detail with reference to the attached drawings.

An embodiment of the present disclosure relates to a laser irradiation device for medical treatment.

FIG. 1 is a block diagram showing a laser irradiation device for medical treatment according to an embodiment of the present disclosure.

Referring to FIG. 1, a laser irradiation device for medical treatment 10 according to an embodiment of the present disclosure includes a handpiece 100, a controller 200, and a display part 300.

The laser irradiation device for medical treatment 10 according to the embodiment of the present disclosure is a device for irradiating a laser treatment target with a laser beam.

In this case, the laser treatment target may refer to a patient, and the laser irradiation device for medical treatment 10 may perform treatment by irradiating a treatment target area of the patient with a laser beam.

To be specific, the laser irradiation device for medical treatment 10 penetrates grid-shaped laser energy into the dermis using a fractional scanner for the purpose of removing skin blemishes and scars, improving wrinkles, and strengthening elasticity.

Fractional means that the laser beam is broken into small pieces, and hundreds to thousands of MTZs (microholes created by laser beams) are created within one square centimeter of skin area. Rather than damaging the whole skin, micro-damaged areas and normal tissue alternately left, so that the damaged tissue is smoothly supplied with cells from surrounding normal epithelial cells, resulting in rapid cell regeneration.

The procedure causes microscopic damage to the treatment area and promotes collagen production, taking advantage of the natural regeneration effect of damaged tissue.

The laser irradiation device for medical treatment 10 according to the embodiment of the present disclosure emits a laser beam in a preset guide shape so as to irradiate only a specific area of the laser treatment target. Since the laser beam may be delivered while accurately distinguishing the damaged area from the normal tissue, the treatment effect may be increased while reducing side effects.

The laser irradiation device for medical treatment 10 according to the embodiment of the present disclosure may include the handpiece 100 and a main body for controlling the handpiece 100, and the controller 200 may be included in the main body.

In this case, the main body may be a computing device that performs the overall steps of receiving data regarding a laser treatment target, setting a guide shape for emitting a laser beam on the basis of the data on the laser treatment target, and generating a control message to control the operation of the handpiece on the basis of the guide shape.

The handpiece 100 is connected to the main body, and receives power from a power source and may emit the laser beam to the treatment target area.

At this time, the handpiece 100 may irradiate the laser treatment target with a laser beam in a preset guide shape.

The handpiece 100 according to the embodiment of the present disclosure may include a scanner 110, an imaging part 120, a motion sensor module 130, and a notification part 140.

The scanner 110 may be disposed inside the handpiece 100, include at least one mirror, and determine the location where the laser beam is emitted on the basis of the preset guide shape.

The scanner 110 may be installed on the inside or outside of the handpiece 100 and provided as an integrated unit, but the present disclosure is not limited to thereto. As another example, the scanner may be provided as separate equipment from the handpiece 100.

The scanner 110 adjusts the irradiation location of the laser beam generated in a light generation part of the handpiece 100.

To be specific, the handpiece may include a light generation part at the front of the scanner 110 and an optical fiber, and the light generation part may generate light (i.e., laser) using power supplied from a power supply part of the main body. The optical fiber is connected to the light generation part, and as the light generated in the light generation part moves through the inside of the optical fiber, the movement of light may be guided. In this case, the light repeats total reflection inside the optical fiber and may travel along the direction in which the optical fiber extends.

Thereafter, the scanner 110 may adjust the angle and location at which the laser is emitted by reflecting the light.

The scanner 110 controls the location where the laser beam is emitted on the basis of a preset guide shape, thereby forming a beam pattern of the required laser shape according to the patient's condition.

At this time, the operation of the scanner 110 may be controlled by the controller 200.

The imaging part 120 is placed on the outside of the handpiece and may acquire medical image data by photographing the face of the laser treatment target.

Figure 2:
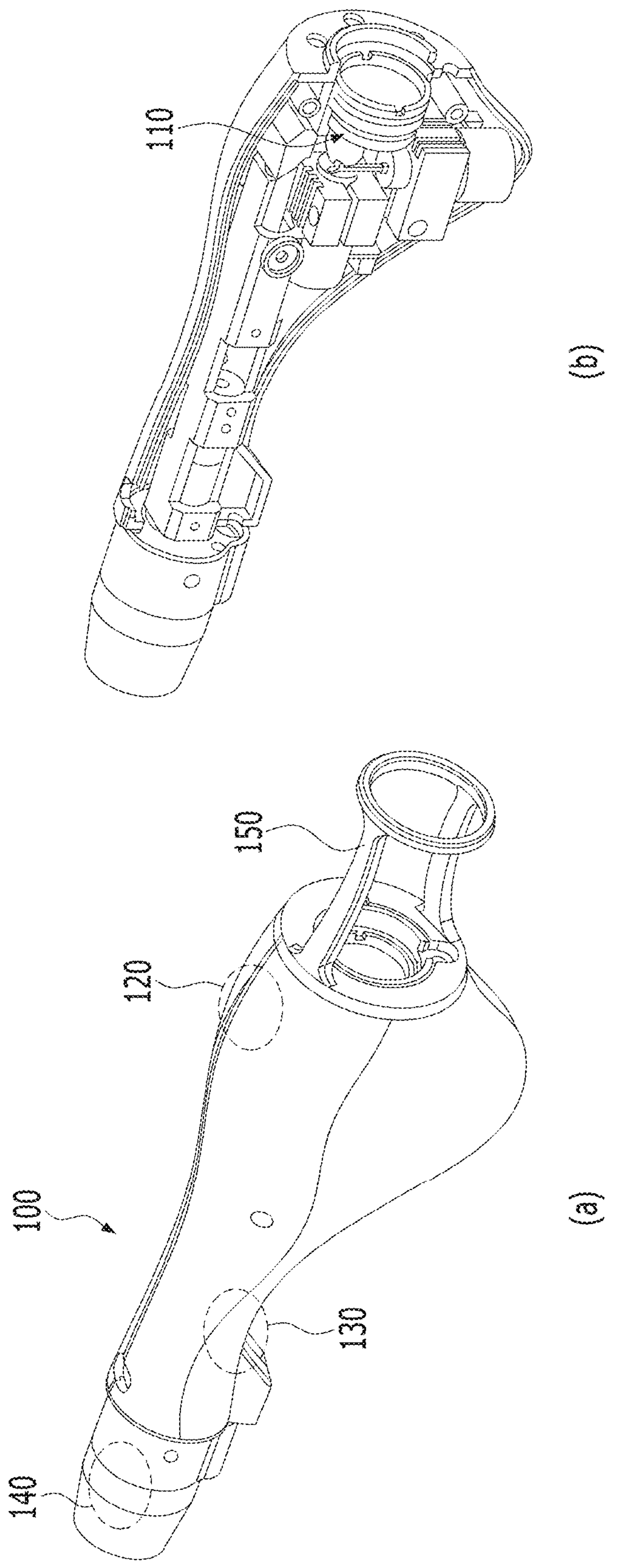
FIG. 2 shows a handpiece of the laser irradiation device for medical treatment according to the embodiment of the present disclosure.

As shown in FIG. 2 below, the imaging part 120 may be located on the outside of the handpiece and photograph the face of the laser treatment target, or may be provided separately from the handpiece and arranged to photograph the laser treatment target.

The imaging part 120 according to the embodiment of the present disclosure is basically equipped with an infrared camera and may further include a color camera. Images captured by the infrared camera and color camera are transmitted to the controller 200 and used to set facial areas as described later, and may be displayed by means of the display part 300.

The motion sensor module 130 is placed on one side of the handpiece and may obtain motion data by detecting movement of the handpiece.

The motion sensor module 130 according to the embodiment of the present disclosure is composed of a geomagnetic sensor, an acceleration sensor, and a gyro sensor to detect position and motion, measure the amount of change in movement state, and may generate motion data by calculating a motion detection result including RAW data for the X, Y, and Z axes, as well as information on azimuth, roll, and pitch from the measured change in movement state.

In addition, the generated motion data may be transmitted to the controller 200 and used by the controller 200 to recognize at least one facial area on which laser treatment has been completed from a plurality of facial areas.

The display part 300 may display the corresponding position of the handpiece on the basis of the face of the treatment target according to the operation of the handpiece.

To be specific, the controller 200 may control a user interface (UI) displayed on the screen to correspond to the motion data, may display the movement of the handpiece on the screen on the basis of the amount of change in the movement state between the first position of the handpiece and the second position of the handpiece after movement.

The notification part 140 is disposed on the outside of the handpiece and may provide notifications using sound or light to the outside.

To be specific, when the position coordinate values of the first facial area where the first laser treatment has been completed and the second facial area where the second laser treatment will be performed after the first laser treatment overlap, the controller 200, which will be described later, may transmit a control message to provide a notification to the notification part, and the notification part 140 disposed on the outside of the handpiece may provide a notification using sound or light to the outside.

The controller 200 may set the guide shape to emit the laser beam and generate a control message to control the operation of the handpiece on the basis of the guide shape on the basis of the data on the laser treatment target.

The controller 200 according to the embodiment of the present disclosure may include at least one processor to control the operation of the handpiece.

In this case, the "processor" may mean, for example, a data processing device built into hardware, which has physically structured circuitry to perform a function expressed by code or instructions contained within a program. Examples of data processing devices built into hardware include processing devices such as microprocessor, central processing unit (CPU), processor core, multiprocessor, application-specific integrated circuit (ASIC), and field programmable gate array (FPGA), but the scope of the present disclosure is not limited thereto.

In addition, according to the embodiment of the present disclosure, the data on the laser treatment target may include at least one of a treatment case of the treatment target that has already been stored or newly input, medical image data of the treatment target, and treatment conditions of the treatment target.

In this case, the treatment case of the treatment target may include laser intensity for treatment, laser irradiation time, and the medical image data of the treatment target may be image data already captured or newly captured by the imaging part 120.

In addition, the treatment conditions of the treatment target may include skin condition and shape of treatment target area of individual patient.

The controller 200 may determine the appropriate irradiation location and set the guide shape for emitting the laser beam depending on individual patient's skin condition included in the data on the laser treatment target and the shape of the treatment target area, etc. Thereafter, the controller may control the handpiece 100 to emit a laser beam based on the set guide shape.

The controller 200 may extract the position coordinate values of individual facial components from the medical image data, and set a plurality of facial areas using the extracted position coordinate values.

The process of setting facial areas will be explained in detail with reference to FIG. 4 below.

Thereafter, the controller 200 may distinguish between the irradiation area and the non-irradiation area from the set facial areas, and in the circular or polygonal laser beam shape, the shape excluding the non-irradiation area may be set as the guide shape for delivering the laser beam.

The process of setting the guide shape for delivering the laser beam will be explained in detail with reference to FIG. 5 below.

Meanwhile, the controller may recognize at least one facial area on which laser treatment has been completed from the plurality of facial areas on the basis of motion data acquired from the motion sensor module 130 of the handpiece.

The process of recognizing at least one facial area on which laser treatment has been completed will be explained in detail with reference to FIG. 6 below.

A memory part 210 stores data regarding the laser treatment target, and in this case, the data regarding the laser treatment target may include at least one of a treatment case of the treatment target that has already been stored or newly input, medical image data of the treatment target, and treatment conditions of the treatment target.

In addition, the memory part 210 may store programs (one or more instructions) for processing and controlling the processor of the controller 200, and may include at least one type of computer-readable storage medium among a flash memory type, a hard disk type, a multimedia card micro type, a card type memory (e.g., SD or XD memory, etc.), random access memory (RAM), static random access memory (SRAM), read-only memory (ROM), electrically erasable programmable read-only memory (EEPROM), programmable read-only memory (PROM), magnetic memory, a magnetic disk, and an optical disk.

The programs stored in the memory part 210 may be divided into a plurality of modules according to function.

The display part 300 may indicate the position of the handpiece corresponding to the face of the treatment target according to the operation of the handpiece.

The display part 300 may match and output medical image data, information about the procedure, and icons according to the operation of the handpiece.

The display part 300 according to the embodiment of the present disclosure includes a display device, and in this case the display device includes all devices with a display function, such as digital TVs and monitors.

A user input part 400 receives a selection input for setting laser treatment conditions from a user in addition to the input for the handpiece 100.

The user input part 400 refers to a means for a user to input data to control a computing device. The user input part 400 may be a key pad, a dome switch, a touch pad (a capacitive overlay, a resistive overlay, an infrared beam, a surface acoustic wave, an integral strain gauge, a piezo electric, etc.), a jog wheel, and a jog switch, but is not limited thereto.

Meanwhile, the main body of the laser irradiation device for medical treatment 10 according to the embodiment of the present disclosure may further include a power part that supplies power to the handpiece 100 to generate a laser emitted to the treatment target area.

The power part is the part that supplies power to the laser generation part and may be disposed inside the main body. may include a battery and a switch. To be specific, the battery that supplies power may be installed inside the main body, and the switch for turning the battery on/off may be placed on the outer surface of the main body. However, the present disclosure is not limited thereto, and as another example, the power part may be disposed outside the main body.

The battery has a battery charging input terminal and may be charged by receiving power from an external source. At this time, the charging status of the battery may be checked through an LED lamp provided on the main body. For example, when the battery is fully charged, the LED lamp blinks green, but when the battery needs to be recharged, the LED lamp blinks red, so that battery charging status may be displayed externally.

FIG. 2 shows a handpiece of the laser irradiation device for medical treatment according to the embodiment of the present disclosure.

A part (a) of FIG. 2 is a view showing the exterior of the laser irradiation device for medical treatment according to the embodiment of the present disclosure, and a part (b) of FIG. 2 is a view showing the interior of the laser irradiation device for medical treatment according to the embodiment of the present disclosure.

Referring to FIG. 2, the handpiece 100 of the laser irradiation device for medical treatment 10 according to the embodiment of the present disclosure includes include the scanner 110, the imaging part 120, the motion sensor module 130, and the notification part 140.

The scanner 110 may be disposed inside the handpiece 100, include at least one mirror, and determine the location where the laser beam is emitted on the basis of the preset guide shape.

The detailed structure of the scanner 110 will be explained in detail with reference to FIG. 7 below.

The scanner 110 may be installed on the inside or outside of the handpiece 100 and provided as an integrated unit, but the present disclosure is not limited to thereto. As another example, the scanner may be provided as separate equipment from the handpiece 100.

The scanner 110 adjusts the irradiation location of the laser beam generated in the light generation part of the handpiece 100.

To be specific, the handpiece may include the light generation part at the front of the scanner 110 and an optical fiber, and the light generation part may generate light (i.e., laser) using power supplied from a power supply part of the main body. The optical fiber is connected to the light generation part, and as the light generated in the light generation part moves through the inside of the optical fiber, the movement of light may be guided. In this case, the light repeats total reflection inside the optical fiber and may travel along the direction in which the optical fiber extends.

Thereafter, the scanner 110 may adjust the angle and location at which the laser is emitted by reflecting the light.

The imaging part 120 is placed on the outside of the handpiece and may acquire medical image data by photographing the face of the laser treatment target.

As shown in FIG. 2 below, the imaging part 120 may be located on the outside of the handpiece and photograph the face of the laser treatment target, or may be provided separately from the handpiece and arranged to photograph the laser treatment target.

The imaging part 120 according to the embodiment of the present disclosure is basically equipped with an infrared camera and may further include a color camera. Images captured by the infrared camera and color camera are transmitted to the controller 200 and used to set facial areas as described later, and may be displayed by means of the display part 300.

The motion sensor module 130 is placed on one side of the handpiece and may obtain motion data by detecting movement of the handpiece.

The motion sensor module 130 according to the embodiment of the present disclosure is composed of a geomagnetic sensor, an acceleration sensor, and a gyro sensor to detect position and motion, measure the amount of change in movement state, and may generate motion data by calculating a motion detection result including RAW data for the X, Y, and Z axes, as well as information on azimuth, roll, and pitch from the measured change in movement state.

In addition, the generated motion data may be transmitted to the controller 200 and used by the controller 200 to recognize at least one facial area on which laser treatment has been completed from a plurality of facial areas.

The display part 300 may display the corresponding position of the handpiece on the basis of the face of the treatment target according to the operation of the handpiece.

To be specific, the controller 200 may control a user interface (UI) displayed on the screen to correspond to the motion data, may display the movement of the handpiece on the screen on the basis of the amount of change in the movement state between the first position of the handpiece and the second position of the handpiece after movement.

The notification part 140 is disposed on the outside of the handpiece and may provide notifications using sound or light to the outside.

To be specific, when the position coordinate values of the first facial area where the first laser treatment has been completed and the second facial area where the second laser treatment will be performed after the first laser treatment overlap, the controller 200, which will be described later, may transmit a control message to provide a notification to the notification part, and the notification part 140 disposed on the outside of the handpiece may provide a notification using sound or light to the outside.

In addition, a contact part 150 that is located at one end of the handpiece and contacts the face of the treatment target may be further included.

Figure 3:
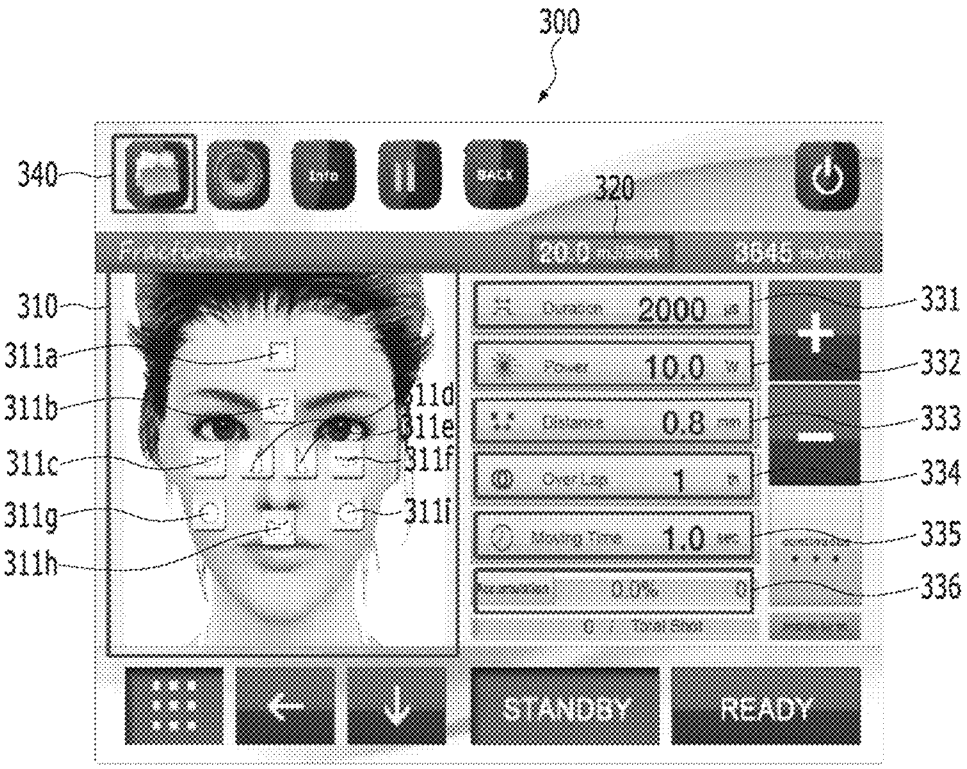
FIG. 3 is a view showing an example of a screen displayed on a display part of the laser irradiation device for medical treatment according to the embodiment of the present disclosure.

FIG. 3 is a view showing an example of a screen displayed on a display part of the laser irradiation device for medical treatment according to the embodiment of the present disclosure.

As shown in FIG. 3, the display part 300 of the laser irradiation device for medical treatment according to the embodiment of the present disclosure may display data on the laser treatment target.

At this time, the data on the laser treatment target may include at least one of a treatment case of the treatment target that has already been stored or newly input, medical image data of the treatment target, and treatment conditions of the treatment target.

Referring to FIG. 3, the display part 300 of the laser irradiation device for medical treatment according to the embodiment of the present disclosure may display the medical image data 310 of the treatment target.

The medical image data 310 may be a frontal facial image taken of the face of the treatment target before the treatment, and the controller 200 determines the shape of laser irradiation area to be irradiated for each part on the basis of the frontal facial image of the face.

As the user selects any of shape buttons (311*a*, 311*b*, 311*c*, 311*d*, 311*e*, 311*g*, 311*h*, and 311*i*) provided for individual parts of the treatment target on a screen that displays medical image data 310, the user may perform treatment by selecting the output shape of the laser and select the appropriate shape for each area to irradiate.

When there is a blind spot or an area that cannot be irradiated, the controller 200 automatically sets the guide shape for emitting the laser beam on the basis of medical image data of the treatment target, eliminating the hassle of the user having to adjust the shape and size to treat blind spots.

Meanwhile, the display part 300 of the laser irradiation device for medical treatment according to the embodiment of the present disclosure may display pulse energy information 320.

In addition, the display part 300 may indicate pulse duration 331 (the time the laser is being emitted) for laser treatment, pulse power 332, a distance 333, overlap settings 334, moving time settings 335, accumulated information 336, etc., and such information may be set in consideration of a treatment case of the treatment target that has already been stored or newly input, and treatment conditions of the treatment target.

In addition, the display part 300 may include a button 340 for checking data information, and the user may load existing information about the treatment target and previous treatment cases by pressing the button 340 to check data information.

Figure 4:
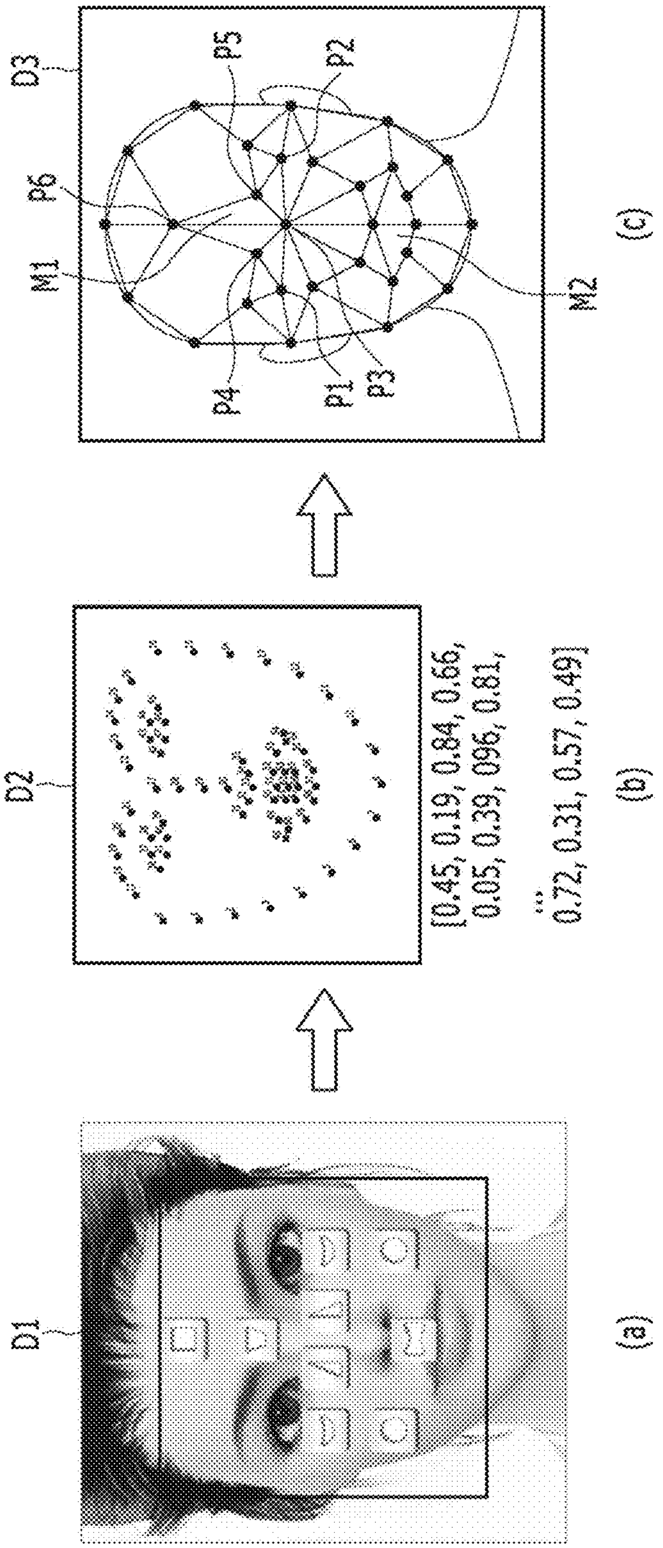
FIG. 4 shows the process by which a controller of the laser irradiation device for medical treatment according to the embodiment of the present disclosure sets facial areas.

FIG. 4 shows the process by which a controller of the laser irradiation device for medical treatment according to the embodiment of the present disclosure sets facial areas.

Referring to FIG. 4, the controller of the laser irradiation device for medical treatment according to the embodiment of the present disclosure may extract the position coordinate values of individual facial components from the medical image data, and set a plurality of facial areas using the extracted position coordinate values.

A part (a) of FIG. 4 shows medical image data acquired by the imaging part 120 of the laser irradiation device for medical treatment according to the embodiment of the present disclosure as an example.

The imaging part 120 captures the face of the laser treatment target and sends the captured image to the controller 200. When there is a previous treatment history, previously captured images may be input from a storage part.

The controller 200 receives medical image data and roughly determines an area D1 where the face is from the medical image data.

At this time, a filter may be used that is able to recognize the area excluding hair and background as the area where the face is.

A part (b) of FIG. 4 shows position coordinate values D2 of facial components extracted from medical image data by the controller 200 of the laser irradiation device for medical treatment according to the embodiment of the present disclosure as an example.

After detecting an approximate face from the input medical image data, the controller 200 may extract specific components within the face, such as eyes, nose, and mouth, and extract the facial area on the basis of the extracted specific components.

For example, if the positions of the two eyes have been detected, the distance between the two eyes may be calculated. Thereafter, the facial area may be extracted as a face image from the input medical image data on the basis of the distance between the two eyes.

In addition, the controller 200 may normalize the size of the facial area using the extracted facial area information. By normalizing the size of the facial area, in the face area, unique features such as the distance between the two eyes and the distance between the eyes and nose may be calculated at the same scale level.

Thereafter, the controller 200 may extract feature information about the face image from the face image. In this case, the feature information refers to information that represents the unique characteristics of a given face included in the face image, and means facial components such as eyes, nose, and mouth. For example, for feature information extraction, techniques including principal component analysis (PCA), linear discriminate analysis (LDA), 2-dimensional principal component analysis (2D-PCA), etc. may be selected and used.

Key coordinates such as eyes, nose, and mouth are extracted from the facial area, and the key coordinates are converted into corresponding numbers.

In addition, various existing technologies may be applied to extract feature information about face images from input medical image data.

A part (c) of FIG. 4 shows as an example a plurality of facial areas D3 set using position coordinate values extracted by the controller 200 of the laser irradiation device for medical treatment according to the embodiment of the present disclosure.

As shown in the part (b) of FIG. 4, after extracting feature information about a face image, facial areas D3 may be divided by connecting the corresponding coordinates.

For example, by connecting a point P1 corresponding to the right eye and a point P2 corresponding to the left eye, a point P3 corresponding to the center between the two eyes may be extracted, and after extracting a point P4 corresponding to the right eyebrow, a point P5 corresponding to the left eyebrow, and a point P6 corresponding to the center of the forehead, an area M1 between the eyebrows may be divided by connecting the point P3 corresponding to the center between the two eyes, the point P4 corresponding to the right eyebrow, the point P5 corresponding to the left eyebrow, and the point P6 corresponding to the center of the forehead.

In addition, an area M2 corresponding to the lips may be divided by connecting the points corresponding to the lips.

Figure 5:
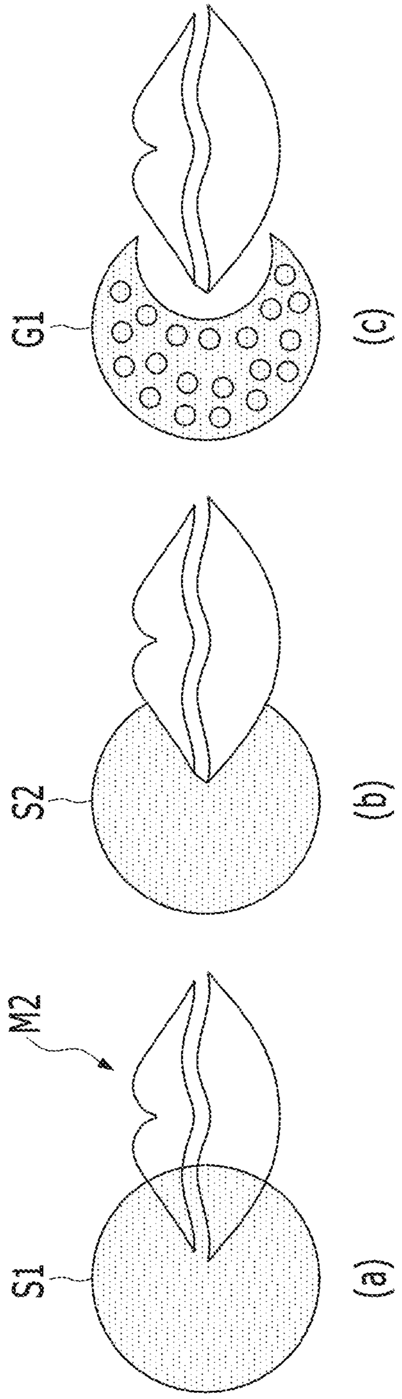
FIG. 5 shows the process by which the controller of the laser irradiation device for medical treatment according to the embodiment of the present disclosure sets a guide shape.

FIG. 5 shows the process by which the controller of the laser irradiation device for medical treatment according to the embodiment of the present disclosure sets a guide shape.

Referring to FIG. 5, the controller 200 of the laser irradiation device for medical treatment according to the embodiment of the present disclosure may distinguish between the irradiation area and the non-irradiation area from the set facial areas, and in the circular or polygonal laser beam shape, the shape excluding the non-irradiation area may be set as the guide shape for delivering the laser beam.

FIG. 5 shows as an example the process of setting a guide shape in the area M2 corresponding to the lips by connecting points corresponding to the lips.

A part (a) of FIG. 5 shows an existing laser irradiation area S1 when the laser is emitted in the area M2 corresponding to the lips.

A part (b) of FIG. 5 shows a non-laser irradiation area S2 in the area M2 corresponding to the lips, where the laser should not be emitted because the area S2 is an actual lip.

When emitting a laser to an area that is difficult to irradiate with a typical square or circle shape, the controller 200 scans the irradiation area before irradiation, determines which areas should be irradiated and which areas should not be irradiated, and creates a new shape.

Thus, as shown in a part (c) of FIG. 5, in the area M2 corresponding to the lips, the shape excluding the non-laser irradiation area S2 from the laser irradiation area S1 may be set as a guide shape G1 for emitting the laser beam.

In addition, the controller 200 controls the scanner of the handpiece so that the laser beam is delivered according to the guide shape G1.

Figure 6:
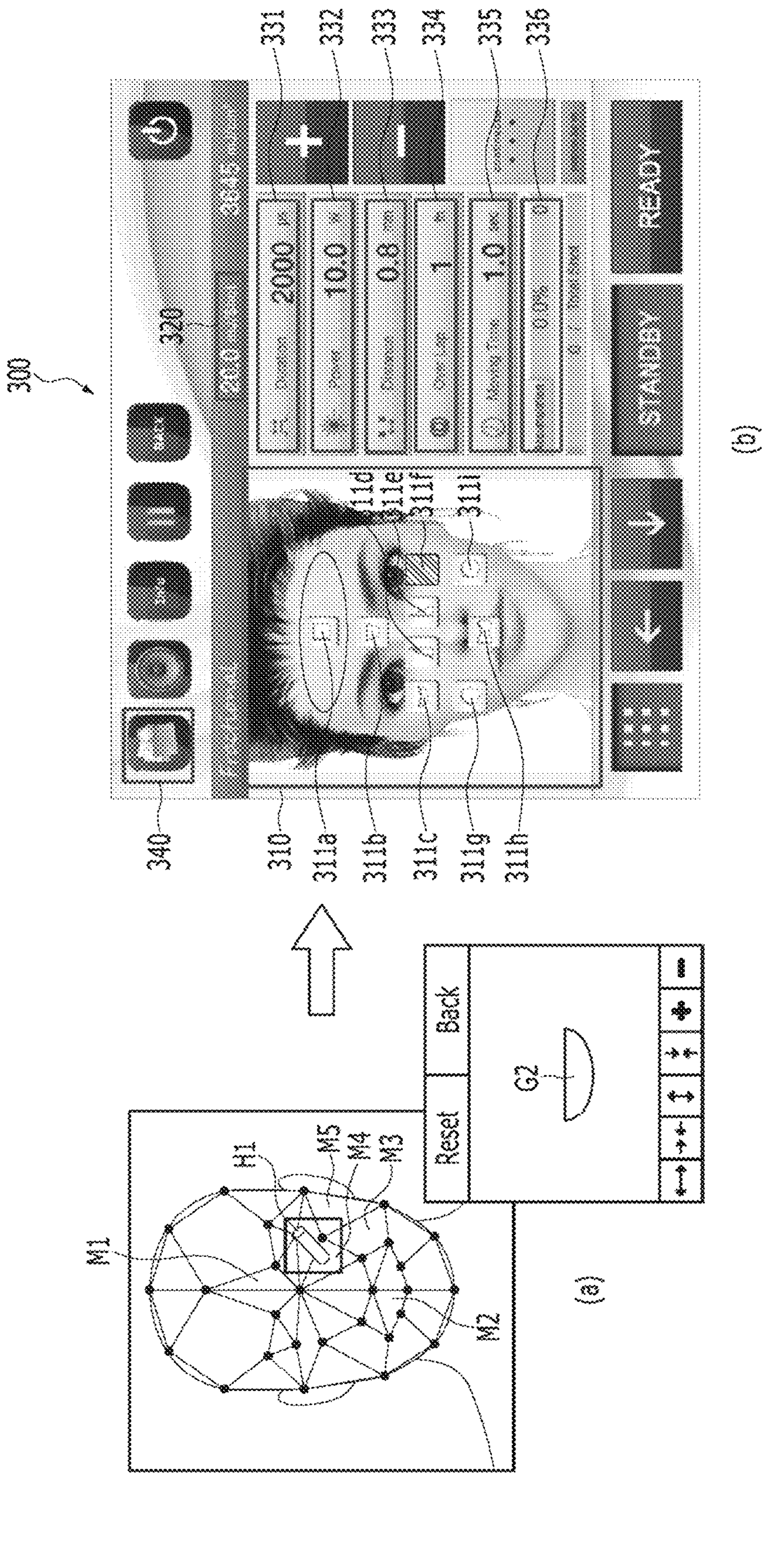
FIG. 6 shows the process by which the controller of the laser irradiation device for medical treatment according to the embodiment of the present disclosure recognizes a facial area where laser treatment has been completed.

FIG. 6 shows the process by which the controller of the laser irradiation device for medical treatment according to the embodiment of the present disclosure recognizes a facial area where laser treatment has been completed.

Referring to FIG. 6, the controller of the laser irradiation device for medical treatment according to the embodiment of the present disclosure may recognize at least one facial area on which laser treatment has been completed from a plurality of facial areas on the basis of motion data acquired from the motion sensor module 130 of the handpiece.

Accordingly, the location where laser irradiation has been completed may be marked with the handpiece to prevent treatments from being performed repeatedly.

To be specific, the motion sensor module 130 is disposed on one side of the handpiece and may acquire motion data by detecting the movement of the handpiece, while the controller 200 receives the motion data and may recognize at least one facial area on which laser treatment has been completed from a plurality of facial areas.

For example, in a part (a) of FIG. 6, when the user selects a cheekbone area M3 of the treatment target and performs the treatment using a handpiece, movement of the handpiece may be detected in that area by means of the motion sensor module 130, and in the display part 300, depending on the operation of the handpiece, a position H1 of the handpiece may be displayed as an icon in the cheekbone area M3 of the treatment target.

In addition, when the treatment area is the cheekbone area M3, a guide shape G2 is changed, and the laser beam may be emitted with the changed guide shape G2.

Thereafter, when the treatment of the cheekbone area M3 of the treatment target is completed, as shown in a part (b) of FIG. 6, among the shape buttons 311*a*, 311*b*, 311*c*, 311*d*, 311*e*, 311*g*, 311*h*, and 311*i* provided for individual areas to be treated, the button 311*f* for the cheek area where the treatment has been completed changes to a different shape on the screen displaying the medical image data 310, and the user may confirm that the treatment in the corresponding area has been completed.

Referring to the part (b) of FIG. 6, since the forehead area has also been treated, the button 311*a* of the forehead area where the treatment has been completed and the surrounding area thereof may also be displayed differently.

Accordingly, during the procedure, an area where the treatment has been completed is indicated by the sensor provided in the handpiece, thereby preventing treatments from being performed repeatedly.

In addition, the controller of the laser irradiation device for medical treatment according to the embodiment of the present disclosure may establish a treatment plan for each area of the plurality of facial areas.

In this case, the treatment plan may be a planned sequence for each of the facial areas so that a first facial area where the first laser treatment is completed and a second facial area where the second laser treatment will be performed after the first laser treatment do not overlap.

To be specific, as shown in the part (a) of FIG. 6, the treatment sequence may be planned for the area corresponding to the eyebrows M1, the area corresponding to the lips M2, the cheekbone area M3, the cheek area M4, and the area corresponding to the sides M5, and the cheek area M4 may be planned to treat after the treatment for the cheekbone area M3 is completed, and at the same time, a guide shape for the cheek area may be prepared.

Meanwhile, when the position coordinate values of the first facial area where the first laser treatment has been completed and the second facial area where the second laser treatment will be performed after the first laser treatment overlap, the controller may transmit a control message to provide a notification to the notification part, and the notification part 140 disposed on the outside of the handpiece may provide a notification using sound or light to the outside.

To be specific, when the controller recognizes that the coordinates of the first facial area where the first laser treatment is completed and the coordinates of the area where the handpiece is located overlap, the controller transmits a control message to the notification part, and the notification part 140 may provide a notification using sound or light to the outside.

Figure 7:
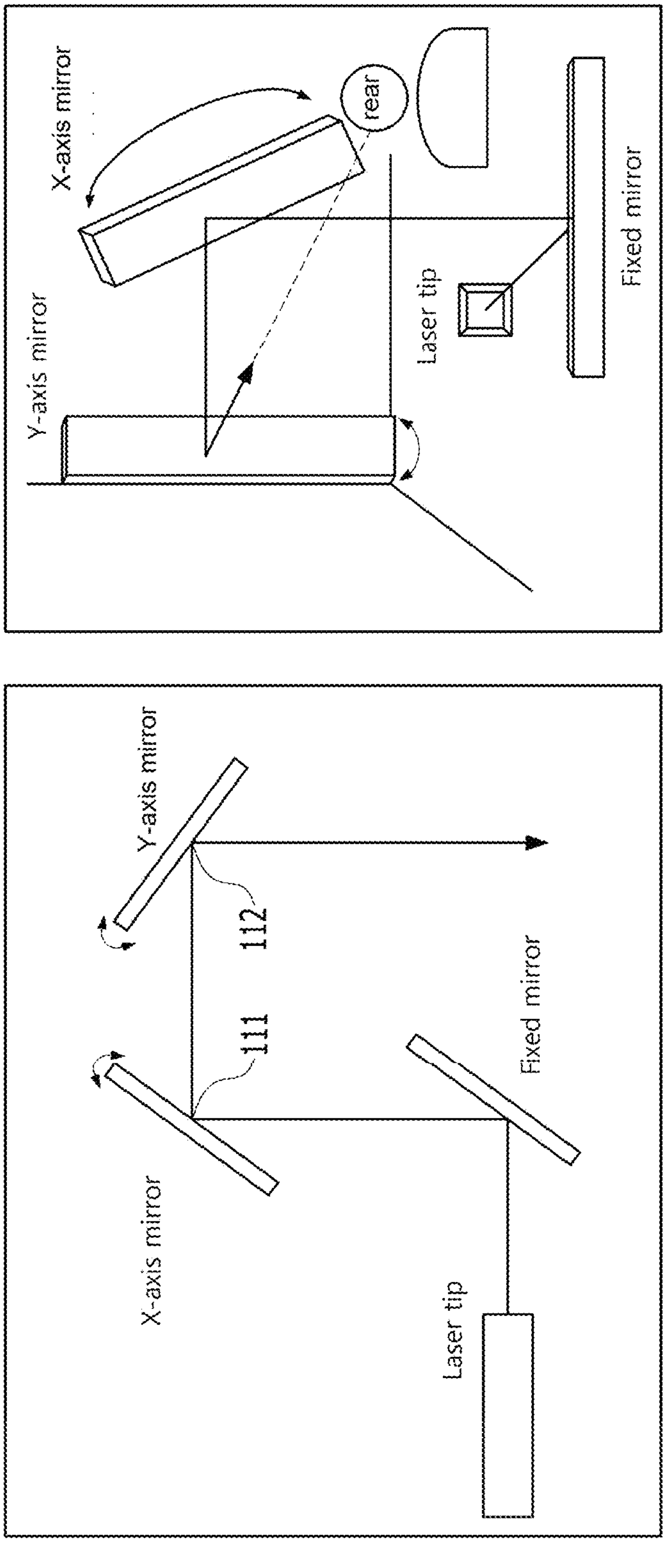
FIG. 7 shows the scanner structure of the handpiece of the laser irradiation device for medical treatment according to the embodiment of the present disclosure.

FIG. 7 shows the scanner structure of the handpiece of the laser irradiation device for medical treatment according to the embodiment of the present disclosure.

Referring to FIG. 7, the scanner 110 of the handpiece of the laser irradiation device for medical treatment according to the embodiment of the present disclosure may further include mirror drive parts 111 and 112 that are connected to the mirror and change the position and angle of the mirror.

Referring to FIG. 7, the scanner 110 of the handpiece of the laser irradiation device for medical treatment according to the embodiment of the present disclosure includes a fixed mirror, an X-axis mirror, and a Y-axis mirror to adjust the location where the laser beam is emitted, and the X-axis mirror and the Y-axis mirror may be rotated by the first mirror drive part 111 and the second mirror drive part 112, respectively.

To be specific, the mirror drive parts may receive a control message from the controller and adjust the position and angle of the mirror to a preset position and angle according to the guide shape.

The first mirror drive part 111 and the second mirror drive part 112 may be implemented as motors (not shown) respectively connected to the center of the X-axis mirror and the center of the Y-axis mirror, or rack-and-pinion type motors (not shown) connected to the sides of the mirrors. The controller may drive the X-axis mirror and Y-axis mirror by controlling the corresponding motor.

By adjusting the height and rotation angle of the X-axis mirror and Y-axis mirror by means of the first mirror drive part 111 and the second mirror drive part 112, the shape of the laser beam may be controlled in various ways.

The foregoing description of the present disclosure is for illustrative purposes only, and a person skilled in the art to which the present disclosure pertains will understand that the present disclosure may be easily modified into another specific form without changing its technical idea or essential features. Therefore, the embodiments described above should be understood in all respects as illustrative and not restrictive. For example, each component described as a single form may be implemented separately. Likewise, components described as separate may also be implemented in a combined form.

The scope of the present disclosure is indicated by the claims described below, and all changes or modifications derived from the meaning and scope of the claims and their equivalent concepts should be construed as being included in the scope of the present disclosure.

What is claimed is:

1. A laser irradiation device for medical treatment for irradiating a laser treatment target with a laser beam, the device comprising:

a handpiece configured to irradiate the laser treatment target with a laser beam in a predetermined laser beam shape, the predetermined laser beam shape being a circular or polygonal shape; and a controller configured to identify position coordinates of individual facial components, including eyes, a nose, and a mouth in a medical image data of a face of the laser treatment target, connect the position coordinates with straight lines, divide the medical image data of the face of the laser treatment target into a plurality of facial areas using the straight lines formed by connecting the position coordinates, each of the plurality of facial areas being in a polygonal shape defined and surrounded by three or more of the straight lines connecting the position coordinates, determine whether each of the plurality of facial areas is a for-irradiation area or a not-for-irradiation area, detect a current position of the handpiece in the medical image data, set a guide shape for emitting the laser beam by adjusting the predetermined laser beam shape in the circular or polygonal shape by geometrically subtracting, from the predetermined laser beam shape, a portion of a facial area, from among the plurality of facial areas, that is determined to be a not-for-irradiation area and that overlaps the predetermined laser beam shape at the detected current position of the handpiece, and generate a control message to control the handpiece to irradiate the laser treatment target with the laser beam in the guide shape.

2. The device of claim 1, wherein the handpiece comprises:

a scanner that is disposed inside the handpiece and includes at least one mirror, the scanner being configured to determine a location where the laser beam is emitted on the basis of the guide shape.

3. The device of claim 2, wherein the handpiece further comprises:

an imaging part that is disposed outside the handpiece, and acquires the medical image data by photographing the face of the laser treatment target; and a motion sensor module that is disposed on a side of the handpiece, detects movement of the handpiece, and acquires motion data.

4. The device of claim 3, wherein the guide shape for emitting the laser beam is set on the basis of data on the laser treatment target, which includes at least one of a treatment case of the treatment target that has already been stored or newly input and treatment conditions of the treatment target.

5. The device of claim 3, wherein the scanner further comprises:

a mirror drive part connected to the mirror configured to change a position and an angle of the mirror, wherein the mirror drive part receives the control message from the controller and adjusts the position and the angle of the mirror to a preset position and angle according to the guide shape.

6. The device of claim 3, wherein the controller recognizes at least one facial area where a laser treatment has been completed from the plurality of facial areas on the basis of the acquired motion data.

7. The device of claim 6, wherein the controller establishes a treatment plan for each area of the plurality of facial areas, wherein the treatment plan is a planned sequence for each of the plurality of facial areas so that a first facial area where a first laser treatment is completed and a second facial area where a second laser treatment will be performed after the first laser treatment do not overlap.

8. The device of claim 6, wherein the handpiece further comprises:

a notification part that is disposed on the outside of the handpiece, and provides notifications to an outside using sound or light, and the controller transmits a control message to the notification part to provide notifications when a position coordinate of a first facial area where a first laser treatment is completed and a position coordinate of a second facial area where a second laser treatment will be performed after the first laser treatment overlap.

9. The device of claim 1, further comprising a display which is configured to display a plurality of icons, each corresponding to one of the plurality of facial areas, and an icon representing a location of the handpiece.

* * * * *